United States Patent
Farazi

(10) Patent No.: US 8,473,068 B2
(45) Date of Patent: *Jun. 25, 2013

(54) SUBCARDIAC THRESHOLD VAGAL NERVE STIMULATION

(75) Inventor: Taraneh Ghaffari Farazi, San Jose, CA (US)

(73) Assignee: Pacesetter, Inc., Sunnyvale, CA (US)

(*) Notice: Subject to any disclaimer, the term of this patent is extended or adjusted under 35 U.S.C. 154(b) by 464 days.

This patent is subject to a terminal disclaimer.

(21) Appl. No.: 12/873,868

(22) Filed: Sep. 1, 2010

(65) Prior Publication Data

US 2010/0331908 A1    Dec. 30, 2010

Related U.S. Application Data

(63) Continuation of application No. 11/330,885, filed on Jan. 11, 2006, now Pat. No. 7,813,805.

(51) Int. Cl.
*A61N 1/36* (2006.01)
*A61N 1/368* (2006.01)

(52) U.S. Cl.
CPC .................................. *A61N 1/368* (2013.01)
USPC ............................................. 607/62; 607/50

(58) Field of Classification Search
USPC ................................................ 607/2, 50, 62
See application file for complete search history.

(56) References Cited

U.S. PATENT DOCUMENTS

| | | | | |
|---|---|---|---|---|
| 3,774,618 A | * | 11/1973 | Avery | 607/118 |
| 4,934,368 A | * | 6/1990 | Lynch | 607/2 |
| 5,320,643 A | * | 6/1994 | Roline et al. | 607/28 |
| 5,330,507 A | * | 7/1994 | Schwartz | 607/14 |
| 5,441,521 A | * | 8/1995 | Hedberg | 607/6 |
| 5,690,681 A | * | 11/1997 | Geddes et al. | 607/2 |
| 5,978,705 A | * | 11/1999 | KenKnight et al. | 607/5 |
| 6,134,470 A | * | 10/2000 | Hartlaub | 607/14 |
| 6,157,862 A | * | 12/2000 | Brownlee et al. | 607/123 |
| 6,341,236 B1 | * | 1/2002 | Osorio et al. | 607/45 |
| 6,473,644 B1 | * | 10/2002 | Terry, Jr. et al. | 607/2 |
| 6,610,713 B2 | * | 8/2003 | Tracey | 514/343 |
| 7,321,793 B2 | * | 1/2008 | Ben Ezra et al. | 607/5 |
| 2004/0038857 A1 | * | 2/2004 | Tracey | 514/1 |
| 2006/0178703 A1 | * | 8/2006 | Huston et al. | 607/2 |

* cited by examiner

*Primary Examiner* — Carl H Layno
*Assistant Examiner* — Luther Behringer
(74) *Attorney, Agent, or Firm* — Steven M Mitchell

(57) ABSTRACT

In one embodiment, an implantable stimulation apparatus includes a vagal nerve stimulator configured to generate electrical pulses below a cardiac threshold of a heart, and an electrode coupled to the vagal nerve stimulator which is configured to transmit the electrical pulses below the cardiac threshold, to a vagal nerve so as to inhibit injury resulting from an ischemia and/or reduce injury resulting from an ischemia. In another embodiment, an implantable stimulation apparatus includes a vagal nerve stimulator configured to generate electrical pulses below a cardiac threshold, and includes an electrode, which is coupled to the vagal nerve stimulator and configured transmit electrical pulses to a vagal nerve so as to reduce a defibrillation threshold of the heart.

20 Claims, 9 Drawing Sheets

SUBCARDIAC THRESHOLD VAGAL NERVE STIMULATION

PRIORITY CLAIM

This application is a Continuation Application of and claims priority and other benefits from U.S. patent application Ser. No. 11/330,885, now issued as U.S. Pat. No. 7,813,805, filed Jan. 11, 2006, entitled "SUBCARDIAC THRESHOLD VAGAL NERVE STIMULATION," incorporated herein by reference in its entirety.

CROSS-REFERENCES TO RELATED APPLICATIONS

The subject matter of the present application is related to U.S. patent application Ser. No. 11/330,884, now issued as U.S. Pat. No. 7,869,869, filed Jan. 11, 2006, entitled "Subcardiac Threshold Vagal Nerve Stimulation" which is herein incorporated by reference in its entirety.

BACKGROUND

Implantable devices for stimulating vagal nerves may be used to treat various medical conditions of a patient. Typically, an implantable device generates electrical pulses and delivers the electrical pulses to a vagal nerve of the patient to treat a particular medical condition. In many cases, this treatment can have the undesired effects of being uncomfortable to the patient, and causing a reduction in the patient's heart beat rate.

One approach to counter the slowing of the patient's heart beat rate is to stimulate the heart with pacing pulses. Thus, the vagal nerve is stimulated to treat the medical condition, and the heart is stimulated to maintain a normal heart beat rate during treatment. Stimulation of the heart during treatment, however, consumes power in the implantable device, which reduces the maximum possible duration for the treatment. Consequently, the medical condition may not be adequately treated with this approach.

In light of the above, there exists a need for stimulating a vagal nerve to treat a medical condition without pacing a patient's heart. There further exists a need for an implantable device that stimulates a vagal nerve for a prolonged period to treat a medical condition.

SUMMARY

In one embodiment, an implantable stimulation apparatus is provided which includes a vagal nerve stimulator configured to generate electrical pulses below a cardiac threshold of a heart. An electrode is coupled to the vagal nerve stimulator and is configured to transmit the electrical pulses, which are below the cardiac threshold, to a vagal nerve so as to inhibit injury resulting from an ischemia and/or reduce injury resulting from an ischemia.

In some implementations, a method is provided which includes generating electrical pulses below a cardiac threshold and treating an ischemia by transmitting the electrical pulses below the cardiac threshold to a vagal nerve.

In another embodiment, an implantable stimulation apparatus is provided which includes a vagal nerve stimulator configured to generate electrical pulses below a cardiac threshold. The implantable stimulation apparatus includes an electrode, which is coupled to the vagal nerve stimulator and configured transmit electrical pulses to a vagal nerve so as to reduce a defibrillation threshold of the heart.

In some implementations, a method is provided which includes generating electrical pulses below a cardiac threshold of a heart and transmitting the electrical pulses to a vagal nerve for reducing a defibrillation threshold of the heart.

DETAILED DESCRIPTION

The following description includes the best mode presently contemplated for practicing the described implementations. This description is not to be taken in a limiting sense, but rather is made merely for the purpose of describing the general principles of the implementations. The scope of the described implementations should be ascertained with reference to the issued claims. In the description that follows, like numerals or reference designators will be used to reference like parts or elements throughout.

There are several potential benefits from subcardiac threshold vagal stimulation. Subcardiac threshold vagal stimulation may be used to inhibit release of pro-inflammatory endotoxins. As such, it is possible to treat ischemia with subcardiac threshold vagal stimulation to reduce, or inhibiting ischemia insult, without the above discussed drawbacks. Furthermore, subcardiac threshold vagal stimulation may be used to reduce the diffibrillation threshold of a patient without the above discussed drawbacks.

Figure 1:
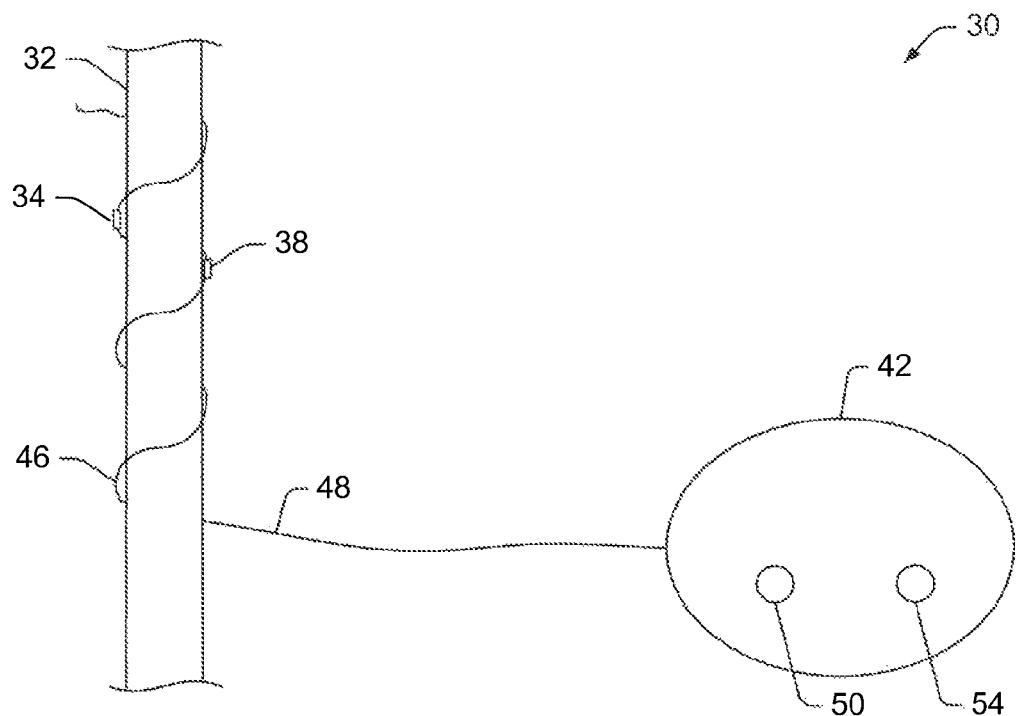
FIG. 1 is a simplified diagram of an embodiment of an implantable subcardiac threshold vagal nerve stimulation apparatus.
Figure 2:
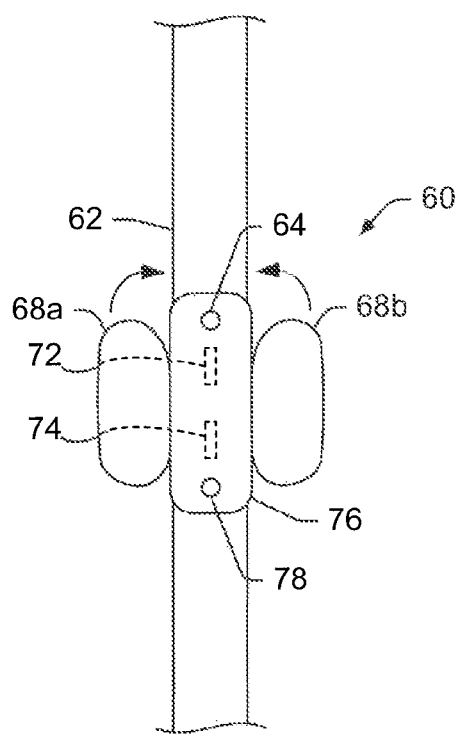
FIG. 2 is a simplified diagram of an embodiment of an additional implantable subcardiac threshold vagal nerve stimulation apparatus.
Figure 3:
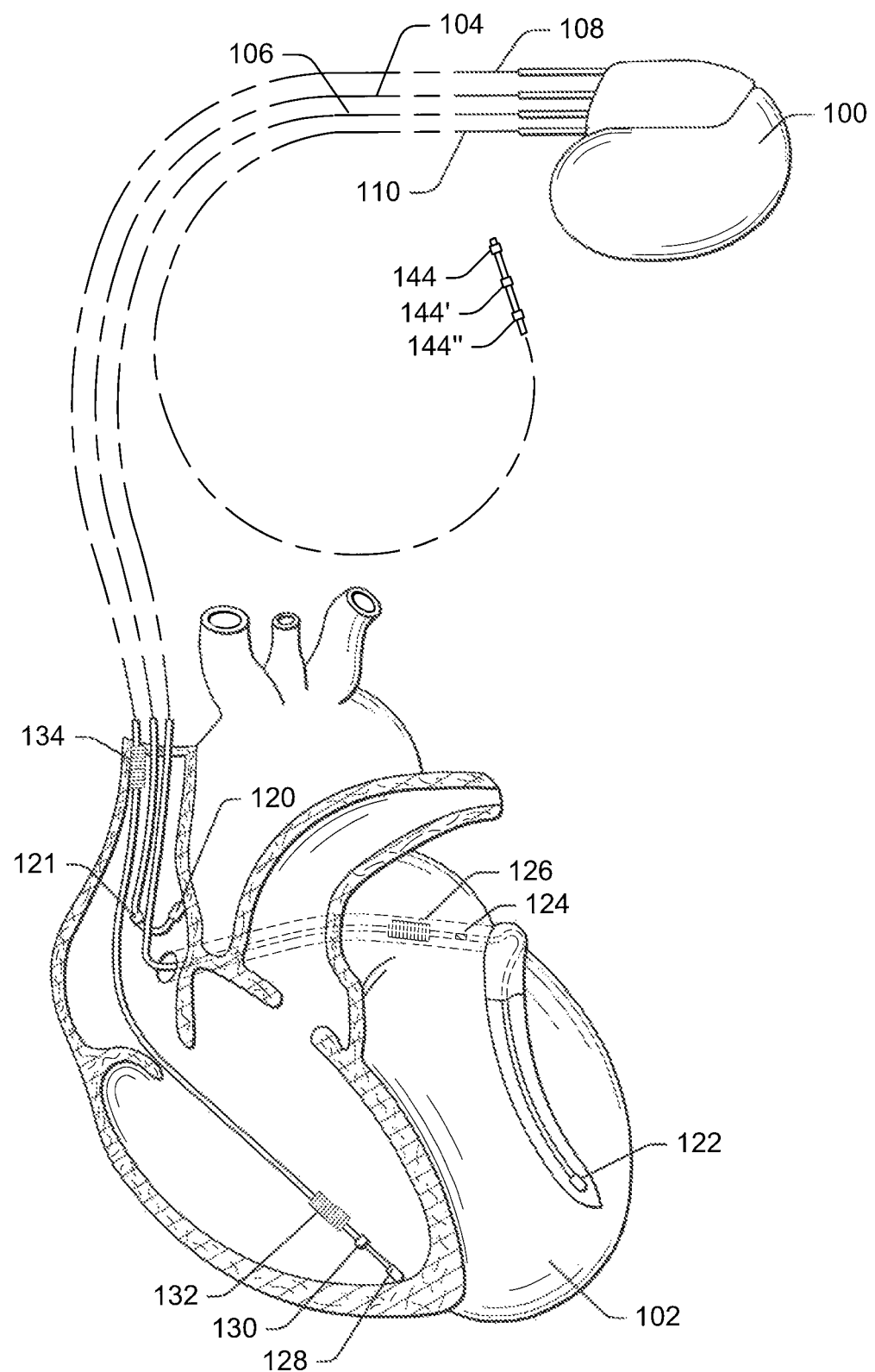
FIG. 3 is a simplified diagram of an embodiment of an implantable subcardiac threshold vagal nerve stimulation apparatus.

FIGS. 1-3 show examples of possible embodiments capable of subcardiac vagal threshold nerve stimulation apparatus in accordance with the present invention. In the embodiment of FIG. 1, an implantable subcardiac threshold vagal nerve stimulation apparatus 1 is coupled in communication via a lead 48 to stimulation electrodes 34 and 38 suitable for subcardiac threshold stimulation of vagal nerve 30 stimulation. In various embodiments, the implantable subcardiac threshold vagal nerve stimulation apparatus 1 includes a means of delivering this energy to anywhere between the cervical and the preganglionic cardiac fibers to provide subcardiac threshold vagal input to the autonomic ganglions, which activates the nicotinic receptors on the post-ganglionic fibers. The implantable subcardiac threshold vagal nerve stimulation apparatus 30 includes a vagal nerve stimulator (shown in FIG. 3), such as a pulse generator that generates low level pulse trains, to stimulate the vagus. In the embodiment of FIG. 1, the stimulation electrodes 34 and 38 are positioned adjacent the vagal nerve 32 with a helical or a cork screw shaped portion 46 of the lead 48, which may be partially or completely wound around the vagal nerve 32. The stimulation electrodes 34 and 38 (or additional electrodes) may be in contact with the vagas nerve to stimulate it directly, or it may be near the vagas nerve and stimulate it indirectly.

In the embodiment shown in FIG. 1, the implatable subcardiac threshold vagal nerve stimulation apparatus 30 includes optional heart activity sensors 50 and 54 capable of sensing for heart activity. As such, the heart sensors 50 and 54 may be electrodes embedded in the case 42 used to capture electrocardiogram signals. In some embodiments, the sensors 50 and 54 may be outside the case 42 and connected by leads (not shown), or wirelessly. The leads may be placed subcutaneously, epicardially, or endocardially. In other embodiments (not shown), the sensors 50 and 54 may be omitted. For example, the sensors may be omitted in some embodiments used to treat ischemia. If used prior to an ischemia, to inhibit injury from the ischemia, the sensing of electrocardiograms may not be necessary to apply therapy.

On the other hand, in some embodiments the sensors such as 50 and 54 may be exploited. For example, in some embodiments adapted to lower the defibrillation threshold during ventricular fibrillation, sensors such as 50 and 54 can provide information for input to an algorithm, which may used to detect the onset of the ventricular fibrillation. If ventricular fibrillation is detected, subcardiac threshold vagal nerve stimulation is activated to reduce the defibrillation threshold, prior to and/or during defibrillation. As such, in yet other embodiments, one or more of the sensors 50 and 54 may be part of one or more endocardial leads, such as shown in FIG. 3. Furthermore, the ability to monitor cardiac activations can provide a feedback mechanism to ensure the stimulation strengths are below the cardiac threshold.

FIG. 2 shows another possible embodiment of an implantable subcardiac threshold vagal nerve stimulation apparatus 60. In the embodiment of FIG. 2, the implantable subcardiac threshold vagal nerve stimulation apparatus 60 includes flexible flaps 68*a* and 68*b* that may be wrapped around the vagal nerve 62, as illustrated by the arrows, to hold the stimulation electrodes 72 and 74 adjacent the vagal nerve 62. Other anchoring mechanisms to secure placement of the electrodes and/or the implantable subcardiac threshold vagal nerve stimulation apparatus 60 by the nerve are possible. The embodiment of FIG. 2 is shown with heart activity sensors 64 and 78 embedded in the case 76.

In various embodiments, the implantable subcardiac threshold vagal nerve stimulation apparatus 60 is capable of sensing cardiac electrical activations, possibly from two, or more, active electrodes on the case 42 or 76, one or more electrodes placed sub-cutaneously with the case as the active electrode, or one or more electrodes placed endocardially/epicardially, with the case 42 or 76 as an active electrode.

Turning to FIG. 3, in one possible embodiment, a subcardiac threshold vagal nerve stimulation apparatus may include, or be part of, a implantable cardiac rhythm management device, or vice-versa. FIG. 3 shows an example implantable stimulation apparatus 100 which includes a subcardiac threshold vagal nerve stimulator (shown in FIG. 4). The implantable stimulation apparatus 100 is coupled via a lead 110 to three electrodes 144, 144', 144" suitable for stimulation of autonomic nerves such as non-myocardial tissue, vagal nerves, or other nerves. For example, the lead 110 may be positioned in and/or near a patient's heart 102 or near an autonomic nerve within a patient's body and remote from the heart 102. The lead 110 optionally includes an exemplary lead portion, as described in further detail below. Although three electrodes 144, 144', and 144" are shown in FIG. 3, the implantable stimulation apparatus 100 may be in electrical communication with the patient's vagal nerves via fewer or more electrodes.

In this embodiment, the implantable stimulation apparatus 100 is shown coupled in electrical communication with the heart 102 via three leads 104, 106, 108, suitable for delivering multi-chamber stimulation and shock therapy. The leads 104, 106, 108 are optionally configurable for delivery of stimulation pulses suitable for stimulation of autonomic nerves, non-myocardial tissue, other nerves, etc. The right atrial lead 104, as the name implies, is positioned in and/or passes through a patient's right atrium. The right atrial lead 104 optionally senses atrial cardiac signals and/or provide right atrial chamber stimulation therapy. As shown in FIG. 3, the implantable stimulation apparatus 100 is coupled to an implantable right atrial lead 104 having, for example, an atrial tip electrode 120, which typically is implanted in the patient's right atrial appendage. The lead 104, as shown in FIG. 3, also includes an atrial ring electrode 121. Of course, the lead 104 may have other electrodes as well. For example, the right atrial lead optionally includes a distal bifurcation having electrodes suitable for stimulation of autonomic nerves, non-myocardial tissue, other nerves, etc. The right atrial lead 104 optionally includes an exemplary lead portion, as described in further detail below.

To sense atrial cardiac signals, ventricular cardiac signals and/or to provide chamber pacing therapy, particularly on the left side of a patient's heart, the implantable stimulation apparatus 100 is coupled to a coronary sinus lead 106 designed for placement in the coronary sinus and/or tributary veins of the coronary sinus. Thus, the coronary sinus lead 106 is optionally suitable for positioning at least one distal electrode adjacent to the left ventricle and/or additional electrode(s) adjacent to the left atrium. In a normal heart, tributary veins of the coronary sinus include, but may not be limited to, the great cardiac vein, the left marginal vein, the left posterior ventricular vein, the middle cardiac vein, and the small cardiac vein.

Accordingly, an exemplary coronary sinus lead 106 is optionally designed to receive atrial and ventricular cardiac signals and to deliver left ventricular pacing therapy using, for example, at least a left ventricular tip electrode 122, left atrial pacing therapy using at least a left atrial ring electrode 124, and shocking therapy using at least a left atrial coil electrode 126. For a complete description of a coronary sinus lead, the reader is directed to U.S. patent application Ser. No. 09/457,277, filed Dec. 08, 1999, entitled "A Self-Anchoring, Steerable Coronary Sinus Lead" (Pianca et al.); and U.S. Pat. No. 5,466,254, "Coronary Sinus Lead with Atrial Sensing Capability" (Helland), which are incorporated herein by reference. The coronary sinus lead 106 further optionally includes electrodes for stimulation of autonomic nerves. Such a lead may include pacing and autonomic nerve stimulation functionality and may further include bifurcations or legs. For example, an exemplary coronary sinus lead includes pacing electrodes capable of delivering pacing pulses to a patient's left ventricle and at least one electrode capable of stimulating an autonomic nerve. An exemplary coronary sinus lead (or left ventricular lead or left atrial lead) may also include at least one electrode capable of stimulating an autonomic nerve, non-myocardial tissue, other nerves, etc., wherein such an electrode may be positioned on the lead or a bifurcation or leg of the lead. A coronary sinus lead 106 optionally includes an exemplary lead portion, as described in further detail below.

The implantable stimulation apparatus 100 is also shown in electrical communication with the patient's heart 102 by way of an implantable right ventricular lead 108 having, in this exemplary implementation, a right ventricular tip electrode 128, a right ventricular ring electrode 130, a right ventricular (RV) coil electrode 132, and a superior vena cava (SVC) coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of sensing or receiving cardiac signals, and delivering stimulation in the form of pacing and shock therapy to the right ventricle. An exemplary right ventricular lead may also include at least one electrode capable of stimulating an autonomic nerve, non-myocardial tissue, other nerves, etc., wherein such an electrode may be positioned on the lead or a bifurcation or leg of the lead. The right ventricular lead 108 optionally includes an exemplary lead portion, as described in further detail below.

Figure 4:
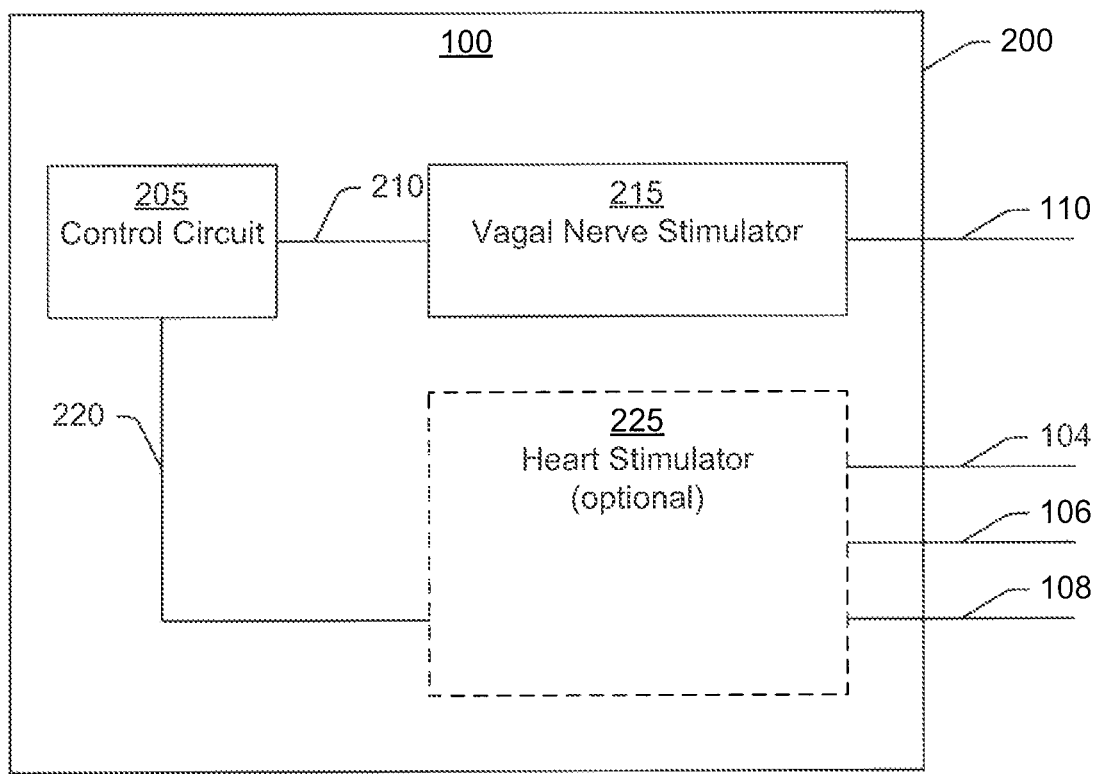
FIG. 4 is a functional block diagram of a possible embodiment of an implantable subcardiac threshold vagal nerve stimulation apparatus.

FIG. 4 shows an exemplary, simplified block diagram depicting various components of the implantable stimulation apparatus 100. The implantable stimulation apparatus 100 includes a housing 200 which may be programmably selected to act as the return electrode in combination with one or more of the electrodes 144, 144', or 144" for electrical stimulation of an autonomic nerve, such as a vagal nerve, or for sensing of cardiac activity occurring in the heart 102 (FIG. 3). The implantable stimulation apparatus 100 includes a vagal nerve stimulator 215 coupled in communication with both a control circuit 205 and the lead 110 (FIG. 3). Optionally, the implantable stimulation apparatus 100 includes a heart stimulator 225 coupled in communication with the control circuit 205, the right atrial lead 104 (FIG. 3), the coronary sinus lead 106 (FIG. 3), and the right ventricular lead 108 (FIG. 3).

The vagal nerve stimulator 215 generates electrical pulses below a cardiac threshold of the heart 102 (FIG. 3) for treating an ischemia of the heart 102, or for reducing a defibrillation threshold of the heart 102. The cardiac threshold is a threshold for energy delivered to the heart 102 above which there is a slowing of the heart rate or the conduction velocity. In operation, the vagal nerve stimulator 215 generates the electrical pulses below the cardiac threshold (i.e., subcardiac threshold electrical pulses) such that the beat rate of the heart 102 is not affected. In one embodiment, the energy of the electrical pulses is just below the subcardiac threshold to provide maximum stimulation to a vagal nerve. The frequency of the electrical pulses may be in a range of 10 to 100 Hz. For example, the frequency of the electrical pulses may be 20 Hz. The voltage amplitude of the electrical pulses may be in a range of 0.5 to 20 V. For example, the voltage amplitude of the electrical pulses may be below 5 V. The pulse width of the electrical pulses may be in a range of 0.1 to 5 msec. For example, the pulse width of the electrical pulses may be 2 msec.

In one embodiment, the energy of the electrical pulses is substantially below the subcardiac threshold to increase the battery life of the vagal nerve stimulator 215 and thus increase the maximum possible duration of treatment or therapy.

Although the function of the vagal nerve stimulator 215 described above is to treat an ischemia, or to reduce a defibrillation threshold of the heart 102, in other embodiments the vagal nerve stimulator 215 may function to treat heart failure, reduce an inflammatory response during a medical procedure, stimulate the release of insulin for treating diabetes, suppress insulin resistance for treating diabetes, or treat an infarction of the heart 102.

The vagal nerve stimulator 215 may also sense cardiac activity occurring in the heart 102 (FIG. 3). Such cardiac activity includes P-waves or R-waves occurring in the heart 102, as well as the beat rate of the heart 102. For example, the vagal nerve stimulator 215 may determine the beat rate of the heart 102 based on the period between successive P-waves, the period between successive R-waves, or the period between a P-wave and a successive R-wave. The vagal nerve stimulator 215 may sense the cardiac activity via the leads 104, 106, 108, or 110 (FIG. 3), or any combination thereof. In various embodiments, the vagal nerve stimulator 215 may also sense the cardiac activity via the case 200 in combination with one or more of the leads 104, 106, 108, or 110.

The electrical pulses generated by the vagal nerve stimulator 215 may be continuous or periodic. An advantage of periodic pulses is that adaptation of the vagal nerve to the electrical pulses is inhibited. For example, the electrical pulses may be generated for a period of 45 seconds every 60 seconds. Alternatively, the electrical pulses may be generated in response to a trigger event. An example of a trigger event is cardiac activity, such as a P-wave or an R-wave, occurring in the heart 102. The electrical pulses may be generated for a period of time subsequent to the trigger event for stimulating the vagal nerve.

The control circuit 205 controls operation of the vagal nerve stimulator 215 via a control signal 210. The control circuit 205 may include digital logic circuits, analog logic circuits, or computer software. For example, the control circuit may be a computing processor, such as a microprocessor or a microcontroller. The control circuit 205 may control the energy of the electrical pulses generated by the vagal nerve stimulator 215. For example, the control circuit 205 may control the energy of the electrical pulses based on cardiac activity occurring in the heart 102 (FIG. 3) such that the electrical pulses do not exceed the subcardiac threshold of the heart 102. In embodiments including the optional heart stimulator 225, the control circuit 205 communicates with the heart stimulator 225 via a communication signal 220. For example, the control circuit 205 may provide data concerning the cardiac activity of the heart to the heart stimulator 225 via the communication signal 220.

The optional heart stimulator 225 generates stimulation pulses for stimulating the heart 102 (FIG. 3), and transmits the stimulation pulses to the leads 104, 106, and 108 (FIG. 3) for stimulating the heart 102. The stimulation pulses may be capable of treating various heart conditions, such as arrhythmias, as is described more fully herein. The heart stimulator 225 may generate the stimulation pulses based on cardiac activity received from the control circuit 205 via the communication signal 220.

Figure 5:
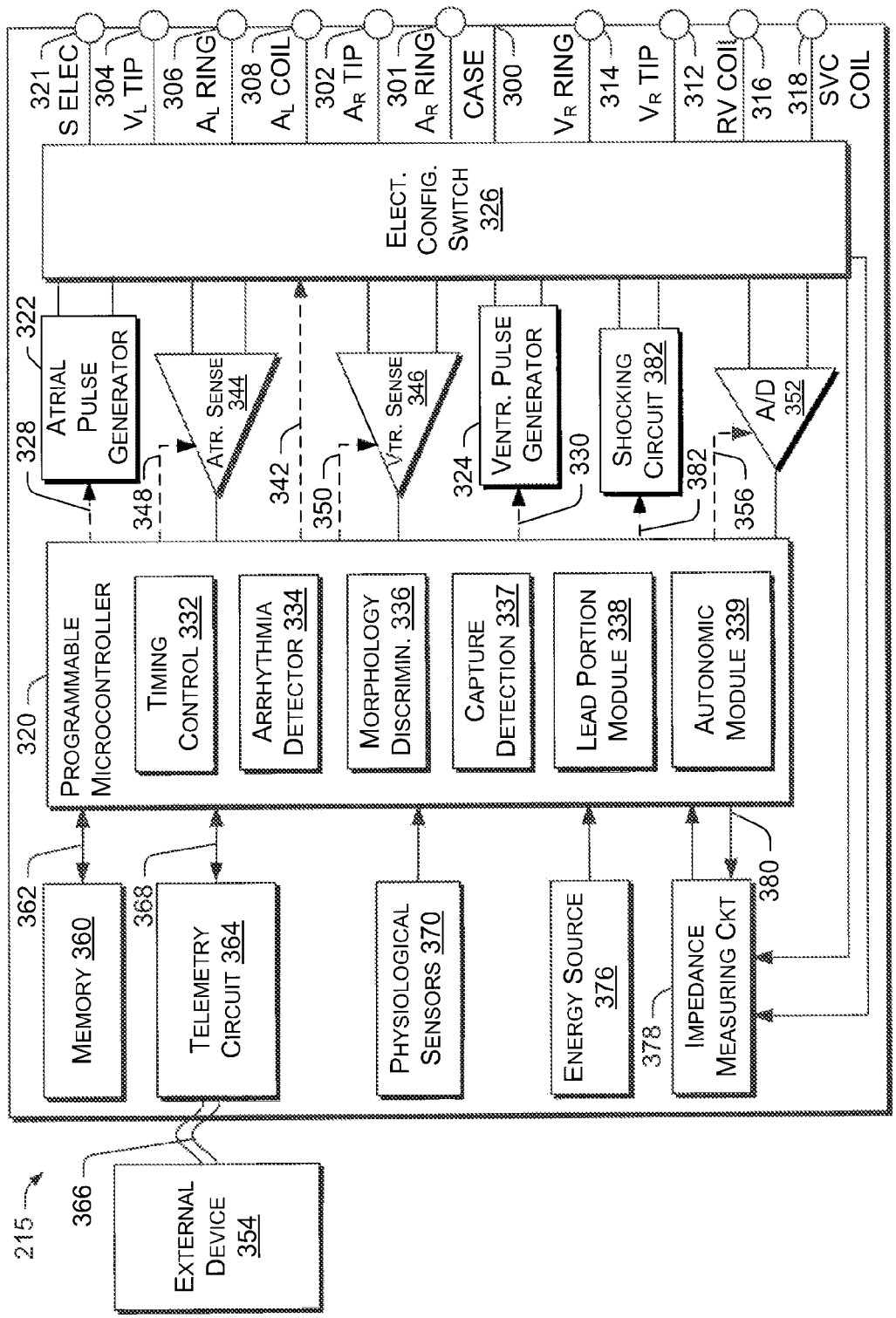
FIG. 5 is a functional block diagram of an exemplary heart stimulator.

FIG. 5 shows an exemplary, simplified block diagram depicting various components of the optional heart stimulator 215. The heart stimulator 215 can be capable of treating both fast and slow arrhythmias with stimulation therapy, including cardioversion, defibrillation, and pacing stimulation. The heart stimulator 215 can be solely or further capable of delivering stimuli to autonomic nerves, non-myocardial tissue, other nerves, etc. While a particular multi-chamber device is shown, it is to be appreciated and understood that this is done for illustration purposes only. Thus, the techniques and methods described below can be implemented in connection with any suitably configured or configurable stimulation device. Accordingly, one of skill in the art could readily duplicate, eliminate, or disable the appropriate circuitry in any desired combination to provide a device capable of treating the appropriate chamber(s) or regions of a patient's heart with cardioversion, defibrillation, pacing stimulation, autonomic nerve stimulation, non-myocardial tissue stimulation, other nerve stimulation, etc.

A housing 200 for the heart stimulator 215 is often referred to as the "can", "case" or "case electrode", and may be programmably selected to act as the return electrode for all "unipolar" modes. Housing 200 may further be used as a return electrode alone or in combination with one or more of the coil electrodes 126, 132 and 134 for shocking purposes. Housing 200 further includes a connector (not shown) having a plurality of terminals 201, 202, 204, 206, 208, 212, 214, 216, 218, 221 (shown schematically and, for convenience, the names of the electrodes to which they are connected are shown next to the terminals).

To achieve right atrial sensing and/or pacing, the connector includes at least a right atrial tip terminal ($A_R$ TIP) 202 adapted for connection to the atrial tip electrode 120. A right atrial ring terminal ($A_R$ RING) 201 is also shown, which is adapted for connection to the atrial ring electrode 121. To achieve left chamber sensing, pacing and/or shocking, the connector includes at least a left ventricular tip terminal ($V_L$ TIP) 204, a left atrial ring terminal ($A_L$ RING) 206, and a left atrial shocking terminal ($A_L$ COIL) 208, which are adapted for connection to the left ventricular tip electrode 122, the left atrial ring electrode 124, and the left atrial coil electrode 126, respectively. Connection to suitable autonomic nerve stimulation electrodes or other tissue stimulation or sensing electrodes is also possible via these and/or other terminals such as a stimulation terminal (S ELEC) 221.

As discussed herein, where an electrode is suitable for stimulation, activation may also be provided using such an electrode. Activation may alter a tissue, for example, to increase permeability of a nerve to thereby cause release of a neurochemical or to change properties of a nerve to thereby decrease or increase its ability to transmit a signal or to release a neurochemical.

To support right chamber sensing, pacing, and/or shocking, the connector further includes a right ventricular tip terminal ($V_R$ TIP) 212, a right ventricular ring terminal ($V_R$ RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively. Connection to suitable autonomic nerve stimulation electrodes or other tissue stimulation or sensing electrodes is also possible via these and/or other terminals such as the stimulation terminal 221.

At the core of the heart stimulator 215 is processor 220 that controls the various modes of stimulation therapy. The processor 220 may be a programmable microcontroller, a microprocessor, or an equivalent control circuitry, designed specifically for controlling the delivery of stimulation therapy, and may further include RAM or ROM memory, logic and timing circuitry, state machine circuitry, and I/O circuitry. Typically, processor 220 includes the ability to process or monitor input signals (data or information) as controlled by a program code stored in a designated block of memory. The type of microcontroller is not critical to the described implementations. Rather, any suitable processor 220 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. No. 4,712,555 (Sholder) and U.S. Pat. No. 4,944,298 (Sholder), all of which are incorporated by reference herein. For a more detailed description of the various timing intervals that may be used within the heart stimulator 215 and their inter-relationship, see U.S. Pat. No. 4,788,980 (Mann et al.), also incorporated herein by reference.

FIG. 4 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart the atrial and ventricular pulse generators, 222 and 224, may include dedicated, independent pulse generators, multiplexed pulse generators, or shared pulse generators. The pulse generators 222 and 224 are controlled by the processor 220 via appropriate control signals 228 and 230, respectively, to trigger or inhibit the stimulation pulses.

The processor 220 further includes timing control circuitry 232 to control the timing of the stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art.

The processor 220 further includes an arrhythmia detector 234, a morphology discrimination module 236, a capture detection module 237, a lead portion module 238, an autonomic module 239 and optionally an orthostatic compensator and a minute ventilation (MV) response module, the latter two are not shown in FIG. 4. These components can be utilized by the heart stimulator 215 for determining desirable times to administer various therapies, including those to reduce the effects of orthostatic hypotension. The aforementioned components may be implemented in hardware as part of the processor 220, or as software/firmware instructions programmed into the heart stimulator 215 and executed on the processor 220 during certain modes of operation.

The lead portion module 238 may perform a variety of tasks related to electrode polarity or electrode selection of an exemplary lead portion. For example, such a module may cause two electrodes to be electrically connected and have a polarity different than a third electrode of an exemplary lead portion. The lead portion module 238 optionally interacts with the autonomic module 239. The autonomic module 239 may determine or otherwise set timings and energy related parameters for activation of an autonomic nerve via an exemplary lead portion, as described further below.

The electronic configuration switch 226 includes a plurality of switches for connecting the desired electrodes to the appropriate I/O circuits, thereby providing complete electrode programmability. Accordingly, switch 226, in response to a control signal 242 from the processor 220, determines the polarity of the stimulation pulses (e.g., unipolar, bipolar, combipolar, etc.) by selectively closing the appropriate combination of switches (not shown) as is known in the art.

An atrial sensing circuit 244 and a ventricular sensing circuit 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial (ATR. SENSE) and ventricular (VTR. SENSE) sensing circuits 244 and 246 may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits 244 and 246 are optionally capable of obtaining information indicative of tissue capture.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the heart stimulator 215 to deal effectively with the difficult problem of sensing the low amplitude signal characteristics of atrial or ventricular fibrillation.

The outputs of the atrial and ventricular sensing circuits 244 and 246 are connected to the processor 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the processor 220 is also capable of analyzing information output from the sensing circuits 244 and 246 and/or the data acquisition system 252 to determine or detect whether capture has occurred and to program a pulse, or pulses, in response to such determinations. The sensing circuits 244 and 246, in turn, receive control signals over signal lines 248 and 250 from the processor 220 for purposes of controlling the gain, threshold, polarization charge removal circuitry (not shown), and the timing of any blocking circuitry (not shown) coupled to the inputs of the sensing circuits 244 and 246.

For arrhythmia detection, the heart stimulator 215 utilizes the atrial and ventricular sensing circuits 244 and 246 to sense cardiac signals to determine whether a rhythm is physiologic or pathologic. In reference to arrhythmias, as used herein, "sensing" is reserved for the noting of an electrical signal or obtaining data (information), and "detection" is the processing (analysis) of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the arrhythmia detector 234 of the processor 220 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

The lead portion module 238 or the autonomic module 239 may operate in conjunction with the arrhythmia detector module 234. For example, the lead portion module 238 may select an electrode polarity for optimal activation of a parasympathetic nerve and the autonomic module 239 may determine energy parameters such as frequency, pulse width, number of pulses in a train, etc., for activation of the parasympathetic nerve. In turn, activation of the parasympathetic nerve via an exemplary lead portion may produce a cardiac response that helps to detect or classify an arrhythmia, for example, in coordination with the arrhythmia detector module 234.

Cardiac signals are also applied to inputs of an analog-to-digital (A/D) data acquisition system 252. The data acquisition system 252 is configured to acquire intracardiac electrogram signals, convert the raw analog data into a digital signal, and store the digital signals for later processing and/or telemetric transmission to an external device 254. The data acquisition system 252 is coupled to the right atrial lead 104, the coronary sinus lead 106, the right ventricular lead 108 and/or the nerve or other tissue stimulation lead 110 through the switch 226 to sample cardiac signals across any pair of desired electrodes.

The processor 220 is further coupled to a memory 260 by a suitable computer bus 262 such as a data/address bus, wherein the programmable operating parameters used by the processor 220 are stored and modified, as required, in order to customize the operation of the heart stimulator 215 to suit the needs of a particular patient. Such operating parameters define, for example, pacing pulse amplitude, pulse duration, electrode polarity, rate, sensitivity, automatic features, arrhythmia detection criteria, and the amplitude, wave shape, number of pulses, and vector of each shocking pulse to be delivered to the patient's heart 102 within each respective tier of therapy. One feature of the described embodiments is the ability to sense and store a relatively large amount of data (e.g., from the data acquisition system 252), which data may then be used for subsequent analysis to guide the programming of the heart stimulator 215.

Advantageously, the operating parameters of the heart stimulator 215 may be non-invasively programmed into the memory 260 through a telemetry circuit 264 in telemetric communication via communication link 266 with the external device 254, such as a programmer, transtelephonic transceiver, or a diagnostic system analyzer. The processor 220 activates the telemetry circuit 264 with a control signal 268. The telemetry circuit 264 advantageously allows intracardiac electrograms and status information relating to the operation of the heart stimulator 215 (as contained in the processor 220 or memory 260) to be sent to the external device 254 through an established communication link 266.

The heart stimulator 215 can further include a physiologic sensor 270, commonly referred to as a "rate-responsive" sensor because it is typically used to adjust pacing stimulation rate according to the exercise state of the patient. The physiological sensor 270 may further be used to detect changes in cardiac output (see, e.g., U.S. Pat. No. 6,314,323, entitled "Heart stimulator determining cardiac output, by measuring the systolic pressure, for controlling the stimulation", to Ekwall, issued Nov. 6, 2001, which discusses a pressure sensor adapted to sense pressure in a right ventricle and to generate an electrical pressure signal corresponding to the sensed pressure, an integrator supplied with the pressure signal which integrates the pressure signal between a start time and a stop time to produce an integration result that corresponds to cardiac output), changes in the physiological condition of the heart, or diurnal changes in activity (e.g., detecting sleep and wake states). Accordingly, the processor 220 responds by adjusting the various pacing parameters (such as rate, AV Delay, V-V Delay, etc.) at which the atrial and ventricular pulse generators, 222 and 224, generate stimulation pulses.

With respect to physiological pressure sensors, commercially available pressure transducers include those marketed by Millar Instruments (Houston, Tex.) under the mark MIKROTIP®. A study by Shioi et al., "Rapamycin Attenuates Load-Induced Cardiac Hypertrophy in Mice", *Circulation* 2003; 107:1664, measured left ventricular pressures in mice using a Millar pressure transducer inserted through the LV apex and secured in the LV apex with a purse-string suture using 5-0 silk. Various exemplary methods, devices, systems, etc., described herein optionally use such a pressure transducer to measure pressures in the body (e.g., chamber of heart, vessel, etc.). Another company, Radi Medical Systems AB (Uppsala, Sweden), markets various lead-based sensors for intracoronary pressure measurements, coronary flow reserve measurements and intravascular temperature measurements. Such sensor technologies may be suitably adapted for use with an implantable device for in vivo measurements of physiology.

While shown as being included within the heart stimulator 215, it is to be understood that the physiologic sensor 270 may also be external to the heart stimulator 215, yet still be implanted within or carried by the patient. Examples of physiologic sensors that may be implemented in the heart stimulator 215 include known sensors that, for example, sense pressure, respiration rate, pH of blood, ventricular gradient, cardiac output, preload, afterload, contractility, and so forth. Another sensor that may be used is one that detects activity variance, wherein an activity sensor is monitored diurnally to detect the low variance in the measurement corresponding to the sleep state. For a complete description of the activity variance sensor, the reader is directed to U.S. Pat. No. 5,476,483 (Bornzin et al.), issued Dec. 19, 1995, which patent is hereby incorporated by reference.

The companies Nellcor (Pleasanton, Calif.) and Masimo Corporation (Irvine, Calif.) market pulse oximeters that may be used externally (e.g., finger, toe, etc.). Where desired, information from such external sensors may be communicated wirelessly to the heart stimulator 215, for example, via an implantable device programmer. Other sensors may be implantable and suitably connected to or in communication with the heart stimulator 215. Technology exists for lead-based oximeters. For example, a study by Tsukada et al., "Development of catheter-type optical oxygen sensor and applications to bioinstrumentation," Biosens Bioelectron, 2003 Oct. 15; 18(12):1439-45, reported use of a catheter-type optical oxygen sensor based on phosphorescence lifetime.

The physiological sensors 270 optionally include sensors for detecting movement and minute ventilation in the patient. The physiological sensors 270 may include a position sensor and/or a minute ventilation (MV) sensor to sense minute ventilation, which is defined as the total volume of air that moves in and out of a patient's lungs in a minute. Signals generated by the position sensor and MV sensor are passed to the processor 220 for analysis in determining whether to adjust the pacing rate, etc. The processor 220 monitors the signals for indications of the patient's position and activity status, such as whether the patient is climbing upstairs or descending downstairs or whether the patient is sitting up after lying down.

The heart stimulator 215 optionally includes circuitry capable of sensing heart sounds and/or vibration associated with events that produce heart sounds. Such circuitry may include an accelerometer as conventionally used for patient position and/or activity determinations. Accelerometers typically include two or three sensors aligned along orthogonal axes. For example, a commercially available micro-electromechanical system (MEMS) marketed as the ADXL202 by Analog Devices, Inc. (Norwood, Mass.) has a mass of about 5 grams and a 14 lead CERPAK (approx. 10 mm by 10 mm by 5 mm or a volume of approx. 500 mm$^3$). The ADXL202 MEMS is a dual-axis accelerometer on a single monolithic integrated circuit and includes polysilicon springs that provide a resistance against acceleration forces. The term MEMS has been defined generally as a system or device having micro-circuitry on a tiny silicon chip into which some mechanical device such as a mirror or a sensor has been manufactured. The aforementioned ADXL202 MEMS includes micro-circuitry and a mechanical oscillator.

The heart stimulator 215 additionally includes an energy source 276 such as a battery that provides operating power to all of the circuits shown in FIG. 4. For the heart stimulator 215, which employs shocking therapy, the energy source 276 is capable of operating at low current drains for long periods of time (e.g., preferably less than 10 μA), and is capable of providing high-current pulses (for capacitor charging) when the patient requires a shock pulse (e.g., preferably, in excess of 2 A, at voltages above 200 V, for periods of 10 seconds or more). The energy source 276 also desirably has a predictable discharge characteristic so that elective replacement time can be detected.

The heart stimulator 215 can further include magnet detection circuitry (not shown), coupled to the processor 220, to detect when a magnet is placed over the heart stimulator 215. A magnet may be used by a clinician to perform various test functions of the heart stimulator 215 and/or to signal the processor 220 that the external programmer 254 is in place to receive or transmit data to the processor 220 through the telemetry circuits 264. Trigger IEGM storage also can be achieved by magnet.

The heart stimulator 215 further includes an impedance measuring circuit 278 that is enabled by the processor 220 via a control signal 280. The known uses for an impedance measuring circuit 278 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds (e.g., heart failure indications such as pulmonary edema and other factors); detecting when the heart stimulator 215 has been implanted; measuring stroke volume; and detecting the opening of heart valves, etc. The impedance measuring circuit 278 is advantageously coupled to the switch 226 so that any desired electrode may be used. The impedance measuring circuit 278 optionally provides information to the lead portion module 238 or the autonomic module 239.

In the case where the heart stimulator 215 is intended to operate as an implantable cardioverter/defibrillator (ICD) device, it detects the occurrence of an arrhythmia, and automatically applies an appropriate therapy to the heart aimed at terminating the detected arrhythmia. To this end, the processor 220 further controls a shocking circuit 282 by way of a control signal 284. The shocking circuit 282 generates shocking pulses in a range of joules, for example, conventionally up to about 40 J, as controlled by the processor 220. Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode).

Cardioversion level shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of approximately 5 J to approximately 40 J), delivered asynchronously (since R-waves may be too disorganized), and pertaining exclusively to the treatment of fibrillation. Accordingly, the processor 220 is capable of controlling the synchronous or asynchronous delivery of the shocking pulses.

In low-energy cardioversion, an ICD device typically delivers a cardioversion stimulus (e.g., 0.1 J, etc.) synchronously with a QRS complex; thus, avoiding the vulnerable period of the T wave and avoiding an increased risk of initiation of VF. In general, if antitachycardia pacing or cardioversion fails to terminate a tachycardia, then, for example, after a programmed time interval or if the tachycardia accelerates, the ICD device initiates defibrillation therapy.

While an ICD device may reserve defibrillation as a latter tier therapy, it may use defibrillation as a first-tier therapy for VF. In general, an ICD device does not synchronize defibrillation therapy with any given portion of a ECG. Again, defibrillation therapy typically involves high-energy shocks (e.g., 5 J to 40 J), which can include monophasic or unidirectional and/or biphasic or bidirectional shock waveforms. Defibrillation may also include delivery of pulses over two current pathways.

Various exemplary methods, devices, systems, etc., described herein pertain to activation of tissue. Various exemplary electrode-bearing lead portions are suitable for placement in a venous structure (e.g., SVC, CS, etc.). Such exemplary lead portions may have a pre-shaped configuration or an adjustable configuration. Such exemplary lead portions include one or more electrodes. In general, such exemplary lead portions include one or more extensions where one extension includes a connector suitable for electrically connecting the lead portion to an implantable device.

Figure 6:
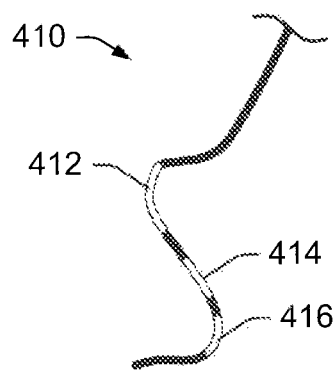
FIG. 6 is a diagram of an exemplary lead portion.

FIG. 6 shows an exemplary electrode-bearing lead portion 410 suitable for positioning in a venous structure such as a vagal nerve. The exemplary lead portion 410 includes a helical configuration. A helix, sometimes also called a coil, is a curve for which the tangent makes a constant angle with a fixed line. The shortest path between two points on a cylinder (one not directly above the other) is a fractional turn of a helix (e.g., consider the paths taken by squirrels chasing one another up and around tree trunks). Helices come in enantiomorphous left- (coils counterclockwise as it "goes away") and right-handed forms (coils clockwise).

A helix is a space curve with parametric equations: $x=r^* \cos(t)$; $y=r^* \sin(t)$; and $z=c^*t$, for t within a range of 0 to $2\pi$, where r is the radius of the helix and c is a constant giving the vertical separation of the helix's loops. Other equations exist to describe arc length, torsion, etc. Other possible configurations include, for example, conical spirals, Poinsot's spirals, polygonal spirals, spherical spirals, semi-spherical spirals, slinky (e.g., spiral wound around a helix), etc.

The lead portion 410 includes a helical configuration that includes three electrodes 412, 414, 416. Such a lead portion may include one or more electrodes. Such electrodes may be controlled by the heart stimulator 215 to act as anodes or cathodes. In general, the configuration acts to help secure the lead portion 410 at a particular location, for example, in a vein.

Figure 7:
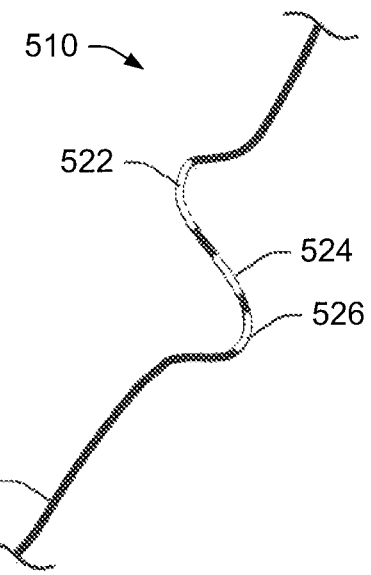
FIG. 7 is a diagram of an exemplary lead portion.

FIG. 7 shows an exemplary electrode-bearing lead portion 510 suitable for positioning in a venous structure such as a vagal nerve. The exemplary lead portion 510 includes a helical configuration. The lead portion 510 includes a helical configuration that includes three electrodes 522, 524, 526 and a distal extension 528. The helical portion may include one or more electrodes and the distal extension 528 may include additional electrodes. Such electrodes may be controlled by the heart stimulator 215 to act as anodes or cathodes. The helical configuration may act to help secure the lead portion 510 at a particular location, for example, in a vein. One or more additional features associated with the distal extension 528 may act to help secure the lead portion 520 at a particular location.

Figure 8:
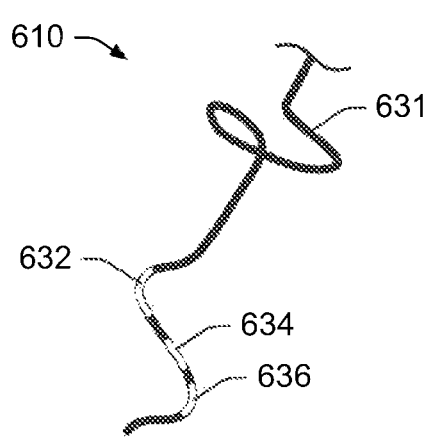
FIG. 8 is a diagram of an exemplary lead portion.

FIG. 8 shows an exemplary electrode-bearing lead portion 610 suitable for positioning in a venous structure such as a vagal nerve. The exemplary lead portion 610 includes a helical configuration. The lead portion 610 includes a securing loop 631 and a helical configuration that includes three electrodes 632, 634, 636. Such a lead portion may include one or more electrodes. Such electrodes may be controlled by the heart stimulator 215 to act as anodes or cathodes. In general, the securing loop 631 acts to help secure the lead portion 610 at a particular location, for example, in a vein.

Figure 9:
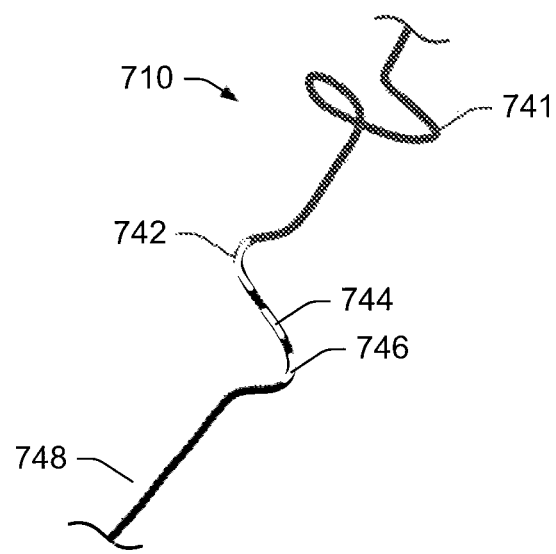
FIG. 9 is a diagram of an exemplary lead portion.

FIG. 9 shows an exemplary electrode-bearing lead portion 710 suitable for positioning in a venous structure such as a vagal nerve. The exemplary lead portion 710 includes a helical configuration. The lead portion 710 includes a securing loop 741, a helical configuration that includes three electrodes 742, 744, 746 and a distal extension 748. The helical portion may include one or more electrodes and the distal extension 748 may include additional electrodes. Such electrodes may be controlled by the heart stimulator 215 to act as anodes or cathodes. In general, the securing loop 741 acts to help secure the lead portion 740 at a particular location, for example, in a vein. One or more additional features associated with the distal extension 748 may act to help secure the lead portion 740 at a particular location.

Figure 10:
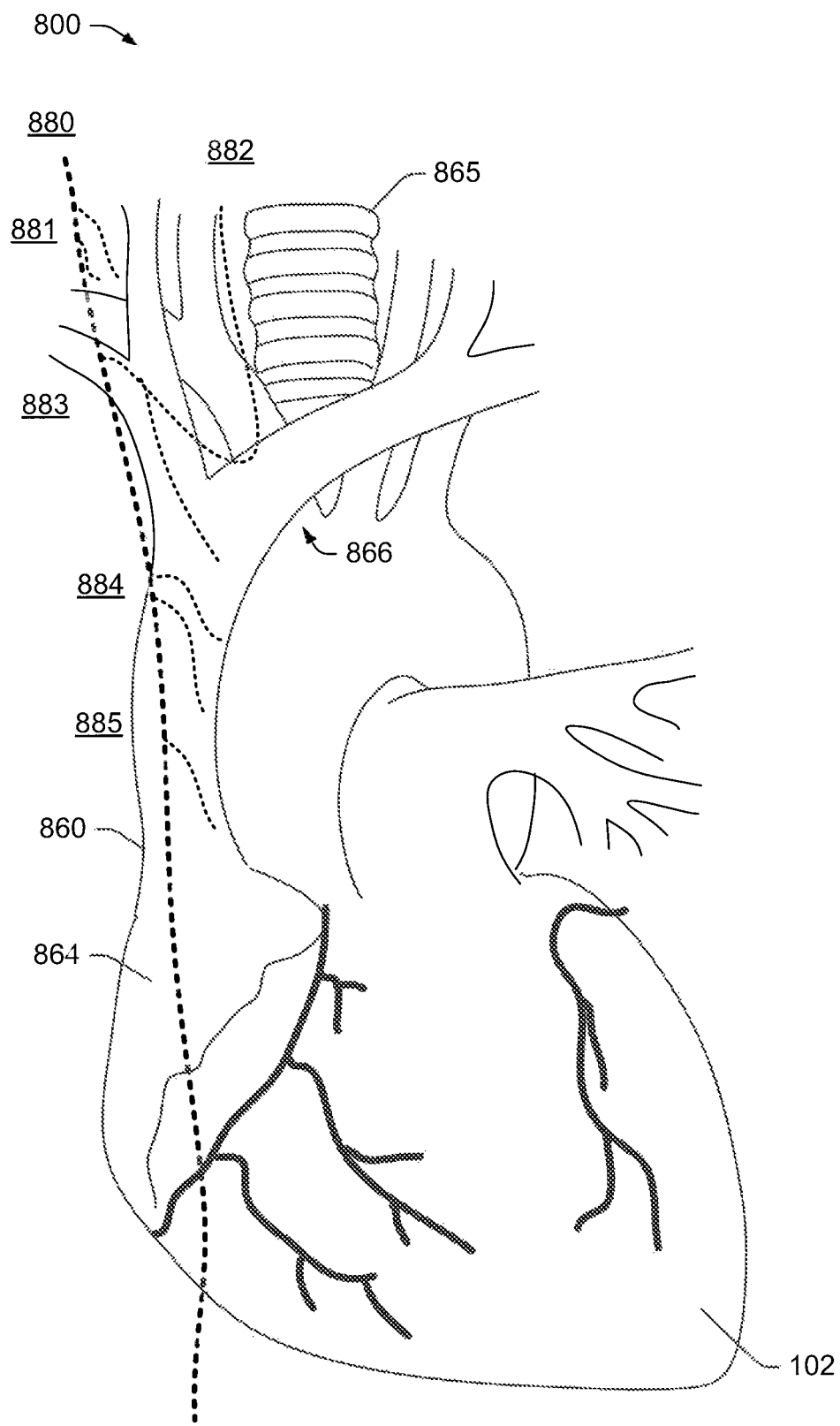
FIG. 10 is an approximate anatomical diagram of the heart and various structures including the right vagal nerve.

As described herein such exemplary electrode-bearing lead portions 410, 510, 610 or 710 may be positioned in a venous structure (e.g., lumen of the structure) and used to activation nerves or tissue. FIG. 10 below shows various nerve pathways with respect to venous structures. In particular, the nerve pathways may have various orientations with respect to the course of a venous structure. Further, depending on the orientation relationship between a nerve and venous structure, selective or optimal activation of the nerve may be achieved using an exemplary electrode-bearing lead portion 410, 510, 610 or 710.

FIG. 10 shows an approximate anatomical diagram 800 that includes the heart 102 and various other structures. In particular, the diagram 800 illustrates the right branch of a vagal nerve 880. The vagal nerve is also known as the vagus nerve or tenth cranial nerve. The vagal nerve 880 is part of the autonomic system and regarded primarily as a parasympathetic nerve. Various autonomic nerve bundles and plexuses exist that include a mixture of parasympathetic and sympathetic nerves.

An article by Kawashima, "The autonomic nervous system of the human heart with special reference to its origin, course, and peripheral distribution", Anat Embryol (2005) 209: 425-438 discloses various nerve pathways including parasympathetic cardiac branches arising from vagus nerve. The Kawashima article classified vagal cardiac branches with direct connections or connections via the cardiac plexus, excluding branches of the lung or surrounding vessels and organs, as follows: superior cardiac branch 881, which arose from the vagus nerve at about the level of the upper (proximal) portion of the recurrent laryngeal nerve branch 882; inferior cardiac branch 883, which arose from the recurrent laryngeal nerve branch 882; and thoracic cardiac branch 884, which arose from the vagus nerve at about the level of the lower (distal) portion of the recurrent laryngeal nerve branch 882.

The diagram 800 shows approximate locations of these branches 881, 883, 884, with respect to the superior vena cava (SVC) 860, the innominate artery 866 (also known as the brachiocephalic trunk), and the trachea 864. The dashed lines indicate that the right vagal nerve 880 and its various branches are not in the fore of the diagram 800 but rather lie generally aft of the SVC 860. Further the dashed lines do not indicate any particular length but rather a general course of such branches as they extend to, or around, the heart and other structures. The diagram 800 illustrates approximate orientation relationships between the venous structures such as the SVC 860 and the right vagal nerve 880 and its various branches. In particular, the orientation relationship between the SVC 860 and the right vagal nerve 880 varies as does the orientation relationship between the SVC 860 and the various branches of the vagal nerve 880.

Kawashima reported that the superior cardiac branch 881 was observed on the right side and the left side (e.g., for the left vagus, not shown), with one to five branches observed in each individual; that the inferior cardiac branch 883 was also observed on the right side and the left side, with one to four branches (average of 2.1 branches; 2.4 right branches, 1.9 left branches); and that the thoracic cardiac branch 884 was observed more so on the right side (18 subjects) compared to the left side (10 subjects), with one to five branches (average of 2.0 branches; 2.6 right branches, 1.4 left branches).

Kawashima reported that the right cardiac plexus usually surrounded the brachiocephalic trunk 866 (which branches into the right subclavian and right carotid arteries), whereas the left cardiac plexus surrounded the aortic arch. Furthermore, the cardiac plexus surrounding the great vessels on both sides was made from a larger cardiac plexus between the aortic arch and the pulmonary arterial trunk through the ventral/dorsal aspect of the aortic arch. On the right side, several nerves were observed passing through the dorsal, rather than the ventral, aspect of the aortic arch. On the left side, no differences between the ventral and dorsal courses to the aortic arch were observed.

Various nerves identified in the Kawashima article extend to one or more epicardial autonomic plexuses. For example, Pauza et al., "Morphology, distribution, and variability of the epicardiac neural ganglionated subplexuses in the human heart", The Anatomical Record 259(4): 353-382 (2000), reported that the epicardial plexus includes seven subplexuses: (I) left coronary, (II) right coronary, (III) ventral right atrial, (IV) ventral left atrial, (V) left dorsal, (VI) middle dorsal, and (VII) dorsal right atrial. The Pauza article states that, in general, the human right atrium is innervated by two subplexuses (III, VII), the left atrium by three subplexuses (IV, V, VI), the right ventricle by one subplexus (II), and the left ventricle by three subplexuses (I, V, VI). The Pauza article also notes that diagrams from Mizeres, "The cardiac plexus in man", Am. J. Anat. 112:141-151 (1963), suggest that "left epicardiac subplexuses may be considered as being formed by nerves derived from the left side of the deep extrinsic cardiac plexus, whereas ventral and dorsal right atrial subplexuses should be considered as being supplied by preganglionated nerves extending from the right vagus nerve and right sympathetic trunk, as their branches course in the adventitia of the right pulmonary artery and superior vena cava". The Pauza article also states that the left coronary (I), right coronary (II), ventral left atrial (IV) and middle dorsal (VI) subplexuses "may be considered as being formed by the deep extrinsic plexus that receives equally from both vagi and sympathetic trunks", With respect to activation of autonomic nerves, end terminals (or terminal knobs) of the postganglionic sympathetic nerves (e.g., epicardial postganglionic sympathetic nerves) release norepinephrine, which can act upon the myocardium. Heart rate, although initially stimulated by norepinephrine, usually decreases over time due to activation of baroreceptors and vagal-mediated (parasympathetic) slowing of the heart rate.

Upon activation, a vagus nerve releases the hormone acetylcholine at its vagal endings and is, therefore, cholinergic. This is in contrast with adrenergic systems which cause the release of epinephrine and norepinephrine. In general, the release of acetylcholine, rather than the passing of nerve impulses, initiates a specific response at an organ (e.g., the heart, etc.), recognizing that parasympathetic input to the brain is typically associated with a more complex mechanism, which may occur depending on stimulation site or stimulation parameters.

Regarding the cardiac branches, parasympathetic vagi nerves are distributed to regions of the sinoatrial (SA) node and the atrioventricular (AV) node where parasympathetic cholinergic muscarinic receptors can act on the SA node to decrease heart rate and act on the AV node to decrease conduction velocity. Release of acetylcholine to these regions typically results in both a decrease in the rate of rhythm of the SA node, as well as a decrease in the cardiac impulse transmission into the ventricles. Consequences of these actions generally include a decrease in heart rate, cardiac output, ventricular contraction, arterial blood pressure, as well as a decrease in overall ventricular pumping.

Electrical stimulation of autonomic nerves has been reported in the literature, see, e.g., Murakami et al., "Effects of cardiac sympathetic nerve stimulation on the left ventricular end-systolic pressure-volume relationship and plasma norepinephrine dynamics in dogs", Jpn. Circ. J. 61(10): 864-71 (1997); and Du et al., "Response to cardiac sympathetic activation in transgenic mice overexpressing beta 2-adrenergic receptor". Am-J-Physiol. Aug; 271(2 Pt 2): H630-6 (1996). Magnetic stimulation of nerves has also been reported, for example, where a nerve is exposed to a time-varying magnetic field, which may induce electrical currents in the nerve.

According to various exemplary technologies described herein, a pulse, a series of pulses, or a pulse train, can be delivered via an exemplary electrode-bearing lead portion, for example, operably connected to heart stimulator 215 to thereby activate an autonomic nerve, other nerve or tissue. The exemplary electrode-bearing lead portion may be used to selectively activate a nerve or optimally activate a nerve through its configuration and optionally through selection of and polarity of one or more electrodes.

A pulse or pulse train optionally includes pulse parameters or pulse train parameters, such as, but not limited to, frequency, pulse duration (or pulse width), number of pulses or amplitude. These parameters may have broad ranges and vary over time within any given pulse train. In general, a power level for individual pulses or pulse trains is determined based on these parameters or other parameters.

Exemplary ranges for pulse frequency for nerve or tissue stimulation include frequencies ranging from approximately 0.1 to approximately 100 Hz, and, in particular, frequencies ranging from approximately 1 Hz to approximately 20 Hz. Of course, higher frequencies higher than 100 Hz may also be suitable. Exemplary ranges for pulse duration, or pulse width for an individual pulse (generally within a pulse train), include pulse widths ranging from approximately 0.01 milliseconds to approximately 5 milliseconds and, in particular, pulse widths ranging from approximately 0.1 milliseconds to approximately 2 milliseconds. Exemplary pulse amplitudes are typically given in terms of current or voltage; however, a pulse or a pulse trains may also be specified by power, charge and/or energy. For example, in terms of current, exemplary ranges for pulse amplitude include amplitudes ranging from approximately 0.02 mA to approximately 20 mA, in particular, ranging from 0.1 mA to approximately 5 mA. Exemplary ranges for pulse amplitude in terms of voltage include voltages ranging from approximately 2 V to approximately 50 V, in particular, ranging from approximately 1 V to approximately 20 V.

Figure 11:
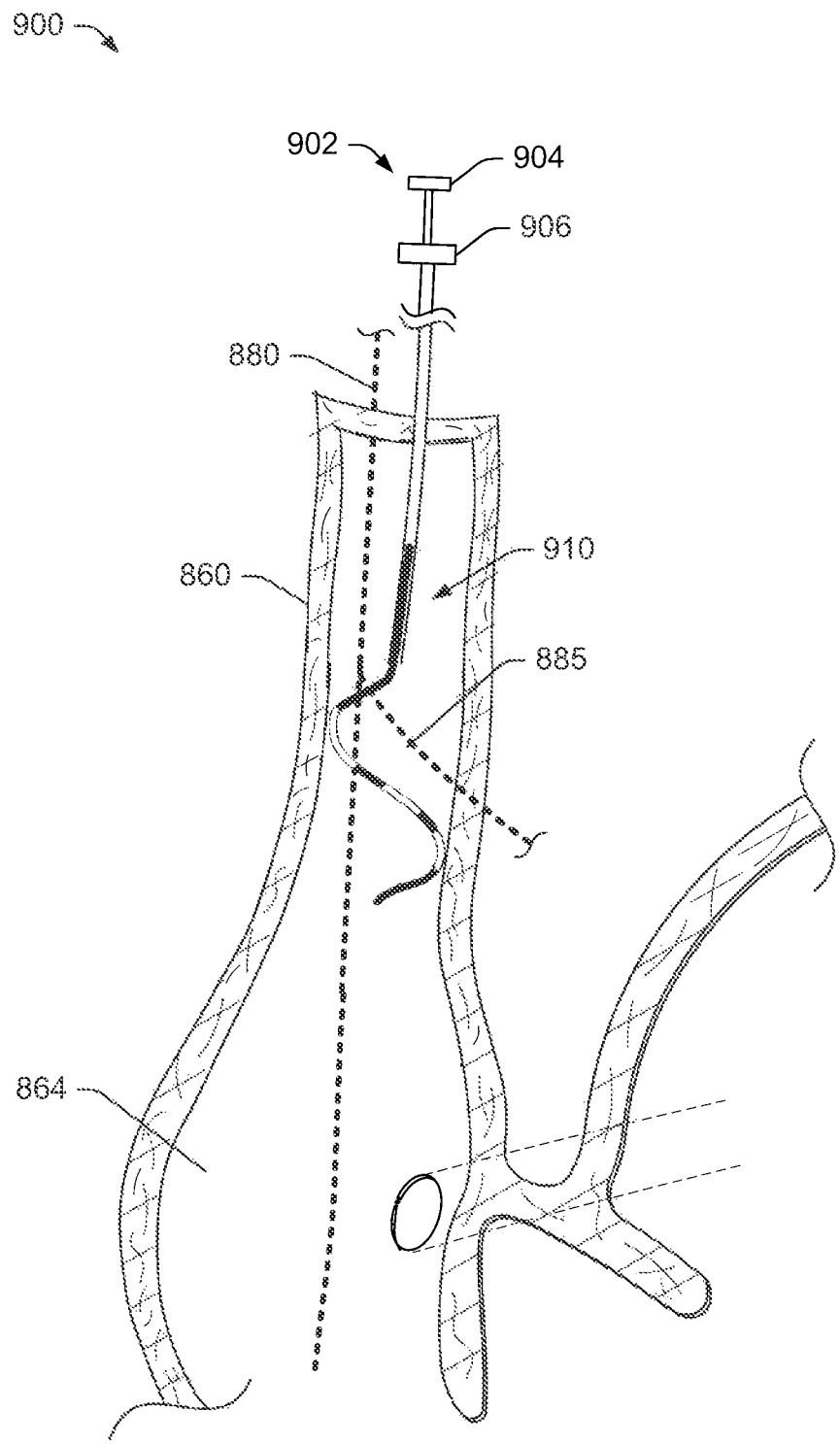
FIG. 11 is a diagram of an exemplary arrangement whereby an exemplary lead portion is positioned in the SVC for activation of a branch of the right vagal nerve.

FIG. 11 shows an exemplary lead 902 positioned in the SVC 860. In this example, the vagal nerve 880 has a right branch 885 that extends at an oblique angle to the lumen of the SVC 860. The lead 902 includes an exemplary lead portion 910 positioned to stimulate the right vagal branch 885. For example, the rotation from the proximal to the distal end of the helix is clockwise so as to position the lead portion 910 primarily along the dorsal wall of the SVC 860 closer to the branch 885 and descending in approximately the same angle as the branch 885. In contrast, a counterclockwise rotation would cause the descending helix to have an angle more orthogonal to the branch 885, as coursing along the dorsal wall of the SVC 860. Thus, given that branches of the right vagal nerve generally descend and are proximate the dorsal or left wall of the SVC, then a clockwise rotation may be preferred should one choose to align the lead portion with such a branch or branches. Should one choose to have an orthogonal orientation proximate to such a branch or branches, then a counterclockwise rotation may be used.

As explained with respect to the examples of FIGS. 4-7, the configuration of the exemplary lead portion 910 contributes to this ability to selectively or optimally activation the desired nerve. One or more other variables may aid in selective or optimal activation of the desired nerve (e.g., stimulation parameters). Further, activation may aim to have a positive or negative effect (e.g., to inhibit or to induce certain action).

The lead 902 includes a mechanism for aid in positioning the lead portion 910 that optionally includes a stylet or pull wire. The exemplary lead 902 is optionally stylet-driven and optionally silicone insulated. The exemplary lead 902 includes one or more electrodes 904 or 906, such as, titanium nitride (TiN) coated platinum-iridium electrodes. Suitable electrodes may be ring, plate (e.g., outwardly directed), or of other shape.

The lead portion 910 is optionally a pre-shaped helix that allows for passive fixation. For example, when a stylet is inserted into the lead portion 910, the lead portion 910 straightens to enhance maneuverability. Complete withdrawal of the stylet from the lead portion 910 allows the pre-shaped helix to press against the walls of the vein and provide some degree of positional stability. Various components of the exemplary arrangement 900 are optionally part of a catheter delivery system for an exemplary lead portion.

While pre-shaping is possible, the lead portion 910 may be optionally shaped in situ through use of a mechanism such as a wire or sheath inserted into the lead portion 910 such that it acquires a helical shape.

A catheter delivery system may include a kink resistant, lubricious sheath, which maintains high radial strength, yet softens in vivo for flexible performance. Peel away features may be used as well as a valve adapter, which can be removed or attached as required, to provide for hemostasis on demand, while reducing air aspiration and back bleeding. An optional sidearm attachment can allow for line flushing and contrast injection. An optional inflatable balloon can create venous back pressure and allow a care provider to block venous flow, for example, to allow for injection of contrast media for visualization of any structure that may aid in the positioning of an exemplary lead portion.

Figure 12:
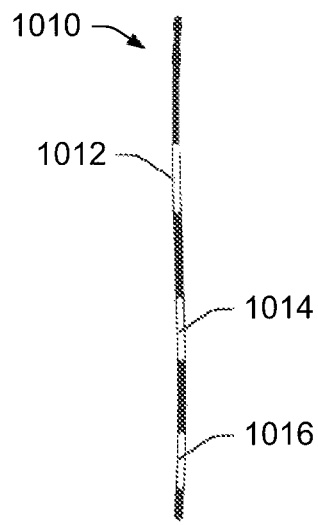
FIG. 12 is a diagram of an exemplary lead portion.

FIG. 12 shows an exemplary lead portion 1010 including one or more electrodes 1012, 1014, 1016. The exemplary lead portion 1010 may be pre-shaped or shaped in situ, either by any of a variety of techniques.

Figure 13:
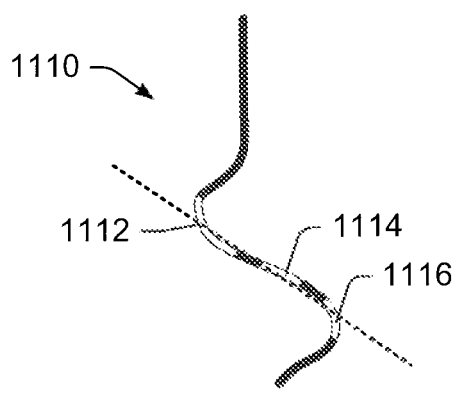
FIG. 13 is a diagram of an exemplary lead portion.

FIG. 13 shows an exemplary lead portion 1110 including one or more electrodes 1112, 1114, 1116. In the exemplary lead portion 1110, the adjacent electrodes 1112, 1114, and 1116 are positioned at an angle of about 34 degrees.

Figure 14:
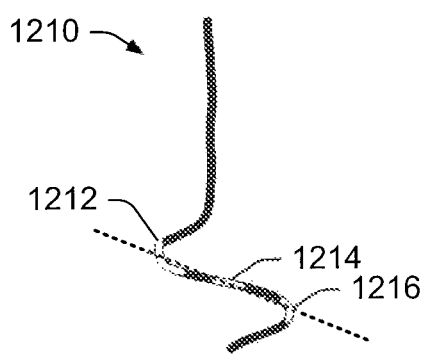
FIG. 14 is a diagram of an exemplary lead portion.

FIG. 14 shows an exemplary lead portion 1210 including one or more electrodes 1212, 1214, 1216. In the exemplary lead portion 1210, the adjacent electrodes 1212, 1214, and 1216 are positioned at an angle of about 22 degrees.

Figure 15:
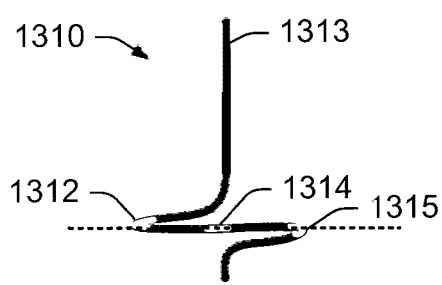
FIG. 15 is a diagram of an exemplary lead portion.

FIG. 15 shows an exemplary lead portion 1310 including one or more electrodes 1312, 1314, 1316. In the exemplary lead portion 1310, the adjacent electrodes 1312, 1314, 1316 are positioned at an angle of about zero degrees (e.g., perpendicular to the proximal end (upper end) of the lead portion 1313.

Figure 16:
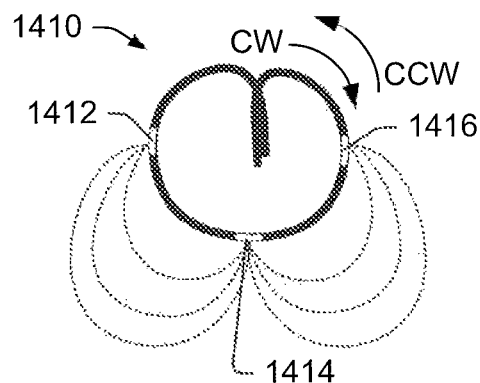
FIG. 16 is a diagram of an exemplary lead portion.

FIG. 16 shows as end view of an exemplary lead portion 1410 including one or more electrodes 1412, 1414, 1416. In the exemplary lead portion 1410, the rotational direction of the helix may be clockwise (CW) or counterclockwise (CCW). Referring again to the example of FIG. 9, the rotation from proximal to distal end of the helix is clockwise so as to position the lead portion 1410 primarily along the dorsal wall of the SVC 860 closer to the branch 885 and substantially parallel to the branch 885. The exemplary lead portion 1410 also shows an exemplary polarity pattern for the three electrodes 1412, 1414, 1416 where the electrode 1414 (e.g., the middle electrode) has a polarity different than that of the electrodes 1412, 1416. Other examples may use other polarities or different number of electrodes.

Figure 17:
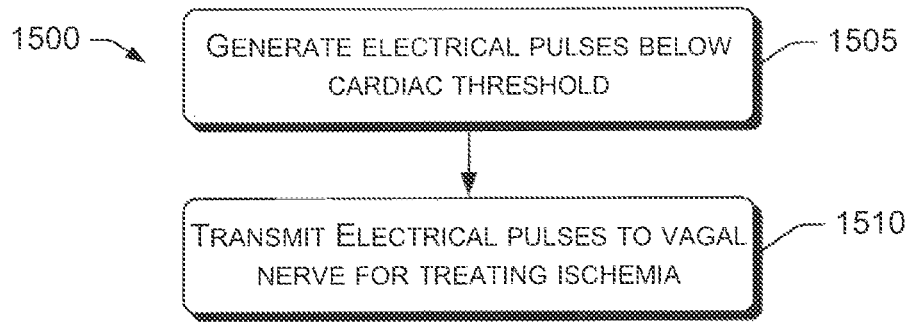
FIG. 17 is a flowchart for a method of treating an ischemia.

FIG. 17 shows a flowchart for an exemplary method 1500 of treating an ischemia of the heart 102 (FIG. 3). In step 1505, electrical pulses are generated below a cardiac threshold (i.e., subcardiac threshold electrical pulses) of the heart 102 (FIG. 3). The energy of the electrical pulses is such that the beat rate of the heart 102 is not reduced. In one embodiment, the vagal nerve stimulator 215 (FIG. 4) generates the electrical pulses and the control circuit 205 (FIG. 4) controls the energy of the electrical pulses. The control circuit 205 may control the frequency, duration, voltage amplitude, current amplitude, pulse width, pulse shape, and timing of the electrical pulses, as is described more fully herein.

In step 1510, the electrical pulses are transmitted to a vagal nerve 880 (FIG. 10) for treating an ischemia of the heart 102 (FIG. 3). In one embodiment, the lead 110 (FIGS. 3 and 4) transmits the electrical pulses to one or more electrodes 144, 144', or 144" (FIG. 3) located in proximity of the vagal nerve 880. The electrodes 144, 144', or 144" may include a lead portion such as lead portion 410 (FIG. 6), lead portion 510 (FIG. 7), lead portion 610 (FIG. 8), lead portion 710 (FIG. 9), lead portion 1210 (FIG. 14), lead portion 1310 (FIG. 15), or lead portion 1410 (FIG. 16). Alternatively, the electrode 144, 144', or 144" may include the lead 902 (FIG. 11).

Figure 18:
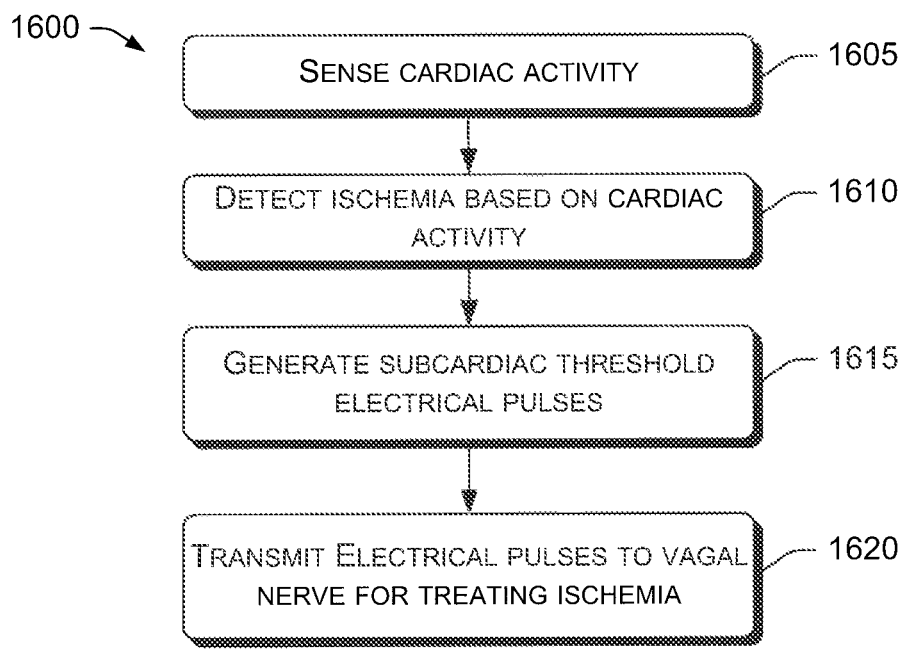
FIG. 18 is a flowchart for a method of treating an ischemia.

FIG. 18 shows a flowchart for an exemplary method 1600 of treating an ischemia of the heart 102 (FIG. 3). In step 1605, cardiac activity of the heart 102 (FIG. 3) is sensed. The sensed cardiac activity may include R-waves or R-waves occurring in the heart 102. In one embodiment, the vagal nerve stimulator 215 (FIG. 4) senses the cardiac activity by receiving electrical signals, which are indicative of the cardiac activity, from one or more of the electrodes 144, 144', or 144" (FIG. 3) via the lead 110 (FIGS. 3 and 4). In a further embodiment, the vagal nerve stimulator 215 also receives these electrical signals via the case 200, which acts as an electrode.

In step 1610, an ischemia of the heart 102 (FIG. 3) is detected based on the sensed cardiac activity. In one embodiment, the control circuit 205 (FIG. 2) detects the ischemia based on the sensed cardiac activity. For example, the control circuit 205 may be a microprocessor or microcontroller programmed to detect the ischemia based on the sensed cardiac activity. One commonly used method to detect ischemic episodes from the heart's electrical activity is to monitor the repolarization. Using the IEGM sensed from electrodes on leads that are positioned either on the device can, subcutaneously, epicardially, endocardially, the ST segment is detected and monitored for any deviation or elevation from it normal baseline level. Another approach is described in U.S. patent application Ser. No. 11/061008 filed on Feb. 17, 2005, entitled "Systems and Methods for Detecting Ischemic Events", herein incorporated by reference.

In step 1615, electrical pulses are generated below a cardiac threshold (i.e., subcardiac threshold electrical pulses) of the heart 102 (FIG. 3). The energy of the electrical pulses is such that the beat rate of the heart 102 is not reduced. In one embodiment, the vagal nerve stimulator 215 (FIG. 4) generates the electrical pulses and the control circuit 205 (FIG. 4) controls the energy of the electrical pulses. The control circuit 205 may control the frequency, duration, voltage amplitude, current amplitude, pulse width, pulse shape, and timing of the electrical pulses, as is described more fully herein.

In one embodiment, the control circuit 205 controls the energy of the electrical pulses based on the cardiac activity. The control circuit 205 may increase the energy of the electrical pulses until the sensed cardiac activity indicates a reduction of the beat rate of the heart 102. The control circuit 205 can then reduce the energy of the electrical pulses to restore the previous heart beat rate. In this way, the control circuit 205 can maximize the energy of the electrical pulses such that the beat rate of the heart 102 is not reduced by the electrical pulses.

In step 1620, the electrical pulses are transmitted to a vagal nerve 880 (FIG. 10) for treating an ischemia of the heart 102 (FIG. 3). In one embodiment, the lead 110 (FIG. 3) transmits the electrical pulses to one or more electrodes 144, 144', or 144" (FIG. 3) located in proximity of the vagal nerve 880. The electrodes 144, 144', or 144" may include a lead portion such as lead portion 410 (FIG. 6), lead portion 510 (FIG. 7), lead portion 610 (FIG. 8), lead portion 710 (FIG. 9), lead portion 1210 (FIG. 14), lead portion 1310 (FIG. 15), or lead portion 1410 (FIG. 16). Alternatively, the electrode 144, 144', or 144" may include the lead 902 (FIG. 11).

Figure 19:
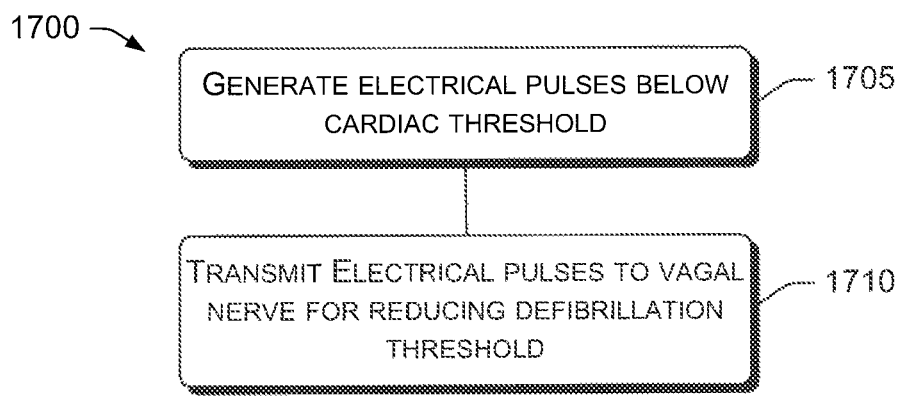
FIG. 19 is a flowchart for a method of reducing a defibrillation threshold.

FIG. 19 shows a flowchart for an exemplary method 1700 of lowering a defibrillation threshold of the heart 102 (FIG. 3). In step 1705, electrical pulses are generated below a cardiac threshold (i.e., subcardiac threshold electrical pulses) of the heart 102 (FIG. 3). The energy of the electrical pulses is such that the beat rate of the heart 102 is not reduced. In one embodiment, the vagal nerve stimulator 215 (FIG. 4) generates the electrical pulses and the control circuit 205 (FIG. 4) controls the energy of the electrical pulses. The control circuit 205 may control the frequency, duration, voltage amplitude, current amplitude, pulse width, pulse shape, and timing of the electrical pulses, as is described more fully herein.

In step 1710, the electrical pulses are transmitted to a vagal nerve 880 (FIG. 10) for reducing a defibrillation threshold of the heart 102 (FIG. 3). In one embodiment, the lead 110 (FIGS. 3 and 4) transmits the electrical pulses to one or more electrodes 144, 144', or 144" (FIG. 3) located in proximity of the vagal nerve 880. The electrodes 144, 144', or 144" may include a lead portion such as lead portion 410 (FIG. 6), lead portion 510 (FIG. 7), lead portion 610 (FIG. 8), lead portion 710 (FIG. 9), lead portion 1210 (FIG. 14), lead portion 1310 (FIG. 15), or lead portion 1410 (FIG. 16). Alternatively, the electrode 144, 144', or 144" may include the lead 902 (FIG. 11).

Although exemplary methods, devices, systems, etc., have been described in language specific to structural features and/or methodological acts, it is to be understood that the subject matter defined in the appended claims is not necessarily limited to the specific features or acts described. Rather, the specific features and acts are disclosed as exemplary forms of implementing the claimed methods, devices, systems, etc.

What is claimed is:

1. An implantable stimulation apparatus comprising:
   a) a vagal nerve stimulator configured to generate electrical pulses having an energy insufficient to slow a patient's heart rate;
   b) a first electrode coupled to the vagal nerve stimulator and configured to transmit the electrical pulses to a vagal nerve so as to at least one of: (1) inhibit injury resulting from an ischemia; or (2) reduce injury resulting from an ischemia;
   c) a second electrode configured to sense cardiac activity of a patient's heart; and
   d) a control circuit coupled to the second electrode and the vagal nerve stimulator, wherein the control circuit: uses the cardiac activity to determine an energy of the electrical pulses at which the patient's heart rate is not slowed; and adjusts energy parameters of the electrical pulses so that the energy of the electric pulses is insufficient to slow the patient's heart rate.

2. The implantable stimulation apparatus of claim 1, wherein the control circuit further detects the ischemia.

3. The implantable stimulation apparatus of claim 1, wherein the control circuit further detects a heart arrhythmia based on the cardiac activity, the implantable stimulation device further comprising:
   a) a third electrode configured to transmit stimulation pulses to the heart; and
   b) a heart stimulator coupled to the third electrode and configured to generate the stimulation pulses for treating the heart arrhythmia.

4. The implantable stimulation apparatus of claim 1, wherein the first electrode comprises at least one of: (a) a flexible flap for wrapping around the vagal nerve; or (b) a helix shape for wrapping around the vagal nerve.

5. The implantable stimulation apparatus of claim 1, wherein the vagal nerve stimulator is configured to supply electrical pulses comprising: (a) a frequency in a range of about 10 Hertz to about 100 Hertz; (b) a pulse width in a range of about 100 microseconds to about 5 milliseconds; (c) a voltage amplitude in a range of 0.5 volts to 20 volts; and (d) a current below 20 milliamps.

6. The implantable stimulation apparatus of claim 5, wherein the vagal nerve stimulator is configured to supply electrical pulses comprising a current below 1 milliamp.

7. The implantable stimulation apparatus of claim 1, wherein the vagal nerve stimulator is configured so as to be capable of supplying electrical pulses comprising at least one of: (a) continuous pulses; (b) periodic pulses; or (c) event triggered pulses.

8. An implantable stimulation apparatus comprising:
   a) a first electrode configured to sense cardiac activity of a heart;
   b) a vagal nerve stimulator configured to generate electrical pulses having an energy sufficient to treat ischemia without slowing of the heart rate;

c) a second electrode coupled to the vagal nerve stimulator and configured to transmit the electrical pulses to a vagal nerve for treating an ischemia; and d) a controller coupled to the first electrode and the vagal nerve stimulator, wherein the controller: controls the vagal nerve stimulator based on the cardiac activity, and reduces the energy of the electrical pulses if the sensed cardiac activity indicates a reduction of the beat rate of the heart.

9. The implantable stimulation apparatus of claim 8, wherein the controller further detects the ischemia based on the cardiac activity.

10. The implantable stimulation apparatus of claim 8, wherein the controller further detects a heart arrhythmia based on the cardiac activity, the implantable stimulation device further comprising:

a) a third electrode configured to transmit stimulation pulses to the heart; and b) a heart stimulator coupled to the third electrode and configured to generate the stimulation pulses for treating the heart arrhythmia.

11. The implantable stimulation apparatus of claim 8, wherein the vagal nerve stimulator is configured so as to be capable of supplying electrical pulses comprising at least one of: (a) continuous pulses; (b) periodic pulses; or (c) event triggered pulses.

12. A method comprising:

determining an energy of electrical pulses sufficient to treat ischemia in a patient without slowing of the patient's heart rate when delivered to a vagal nerve;

generating electrical pulses having said energy sufficient to treat ischemia in a patient without slowing of the patient's heart rate; and treating an ischemia by transmitting the electrical pulses to the vagal nerve.

13. The method of claim 12, wherein treating the ischemia comprises transmitting the electrical pulses to the vagal nerve to reduce injury resulting from the ischemia.

14. The method of claim 12, wherein treating the ischemia comprises transmitting the electrical pulses to the vagal nerve to inhibit injury resulting from the ischemia.

15. The method of claim 12, further comprising:

sensing cardiac activity of the heart, wherein the energy of the electrical pulses is determined based on the cardiac activity.

16. The method of claim 12, wherein the electrical pulses have: (a) a frequency in a range of 10 Hertz to 100 Hertz (b) a pulse width in a range of 100 microseconds to 5 milliseconds; (c) a voltage amplitude in a range of 0.5 volts to 20 volts; and (d) a current below 20 milliamps.

17. The method of claim 6, wherein the electrical pulses have a current below 1 milliamp.

18. The method of claim 12, wherein the electrical pulses are periodic electrical pulses.

19. A method comprising:

sensing cardiac activity of a heart;

detecting an ischemia based on the cardiac activity;

determining an energy of electrical pulses effective to treat ischemia in a patient when delivered to a vagal nerve without slowing of the patient's heart rate based on the cardiac activity of the patient;

generating electrical pulses having an energy sufficient to treat ischemia in a patient without slowing of the patient's heart rate; and transmitting the electrical pulses having said energy sufficient to treat ischemia in a patient without slowing of the patient's heart rate to the vagal nerve for treating an ischemia.

20. The method of claim 19, further comprising controlling the energy of the electrical pulses based on the cardiac activity.

* * * * *